United States Patent [19]

Kirk, III et al.

[11] Patent Number: 5,145,840

[45] Date of Patent: Sep. 8, 1992

[54] TREATMENT OF IDIOPATHIC THROMBOCYTOPAENIC PURPURA

[75] Inventors: Leone E. Kirk, III; Dannie H. King, both of Raleigh; Richard H. Clemons, Cary; Sandra N. Lehrman, Durham; David W. Barry, Chapel Hill, all of N.C.

[73] Assignee: Burroughs Wellcome Co., Research Triangle Park, N.C.

[21] Appl. No.: 679,236

[22] Filed: Apr. 2, 1991

Related U.S. Application Data

[63] Continuation of Ser. No. 877,284, Jun. 23, 1986, abandoned.

[51] Int. Cl.$^5$ .............................................. A61K 31/70
[52] U.S. Cl. ........................................ 514/49; 514/50
[58] Field of Search ..................................... 514/49, 50

[56] References Cited

U.S. PATENT DOCUMENTS 3,817,982  6/1974  Verheyden et al. ............... 536/23

OTHER PUBLICATIONS

J. Montaner, et al., J Acq Imm. Synd. 3:565-570, 1990.

Primary Examiner—John W. Rollins
Attorney, Agent, or Firm—Donald Brown; Lawrence Neilsen

[57] ABSTRACT

A method of treating idiopathic thrombocytopaenia purpura with 2',3'-dideoxy-3'-azidonucleosides, in particular 3'-azido-3'-deoxythymidine, is disclosed.

5 Claims, No Drawings

TREATMENT OF IDIOPATHIC THROMBOCYTOPAENIC PURPURA

This is a continuation of copending application Ser. No. 06/877,84 filed on Jun. 23, 1986, now abandoned.

The present invention relates to 2',340-dideoxy-3'-azido-nucleosides and their use for the treatment or prophylaxis of certain viral and bacterial infections.

Acquired immune deficiency syndrome (AIDS) is an immunosuppressive or immunodestructive disease that predisposes subjects to fatal opportunistic infections. Characteristically, AIDS is associated with a progressive depletion of T-cells, especially the helper-inducer subset bearing the OKT[4] surface marker.

Human T-cell lyphotropic retrovirus HTLV-III has been reproducibly isolated from patients with AIDS or with signs and symptoms that frequently precede AIDS. HTLV-III, unlike HTLV-I or HTLV-II, is cytopathic and appears to preferentially infect and destroy OKT[4]-bearing T-cells. It is now believed that HTLV-III is the etiologic agent of AIDS.

Certain conditions are frequently associated with AIDS but may be treated separately. An example of such a condition is thrombocytopsenia purpura. Thrombocytopsemia is generally characterised by a blood platelet count of below 100,000 mm$^{-3}$. Such low platelet numbers can lead to post-traumatic haemorrhage and very low counts are often associated with spontaneously haemorrhaging which can lead to death is located in the brain or heart.

We have now discovered that a broad class of 2',3'-dideoxy-pyrimidine nucleosides characterised by the presence of an azido group in the 3'-position, and particularly those referred to below are useful for the treatment or prophylaxis of AIDS and related conditions as well as other viral and bacterial infections.

Examples of such 2',3'-dideoxy-3'-azido-nucleosides include those having the following formula:

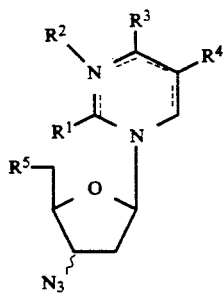

wherein
R$^1$ is hydroxy, mercapto, amino, alkylthio, aralkoxy, alkoxy, cyano or alkylamino;
R$^2$ is hydrogen, acyl, alkyl or sulphonate;
R$^3$ is hydroxy mercapto, amino, triazolo, alkylamino, arylalkoxy, alkoxy or alkylthio;
R$^4$ is alkyl, halo, perhalomethyl, hydroxy, alkylthio, cyano, nitro, alkenyl, halo-substituted alkenyl, alkynyl or hydrogen; and
R$^5$ is hydroxy or mercapto; and pharmaceutically acceptable derivatives thereof including esters and salts and other compounds that are bioprecursors of the compounds of formula (I) or are capable of hydrolysis thereto.

Preferred esters of the compounds of formula (I), particularly when X represents an oxygen atom, include acyl esters such as straight or branched chain alkyl (e.g. $C_{1-18}$ alkyl), aralkyl (e.g. phenylacetyl), aryl (e.g. benzoyl optionally substituted by halogen, $C_{1-4}$ alkyl and/or $C_{1-4}$ alkoxy), organosulphonyl (e.g. methanesulphonyl) and mono-, di-or tri-phosphate esters as well as the corresponding thio esters including dithiocarbamoyl e.g. dialkyl (e.g. methyl) carbamoyl esters.

Examples of pharmaceutically acceptable salts of the compounds of formula (I) include base salts, e.g. derived from an appropriate base, such as alkali metal (e.g. sodium) or alkaline earth metal salts.

in the above general formula (I), the dotted lines in the 2- to 6-positions are intended to indicate single or double ring bonds in these positions in the pyrimidine ring, the relative positions of the single and double bonds being determined by whether the substituents R$^1$ and R$^3$ are groups capable of e.g. keto-enol tautomerism.

Compounds of the present invention have been found to be active against the following diseases: virus infections caused by animal and human retroviruses including T-cell lymphotropic retroviruses (HTLV), especialy HTLV-III and other AIDS-associated viruses including lymphodenopathy-associated virus (LAV), feline leukaemia virus, equine infectious anaemia virus and other lantiviruses, and other human viruses such as non-A, non-B hepatitis virus, hepatitis B virus, Epstein-Barr virus (EBV) and cytomegalovirus (CMV); and certain bacterial infections caused by such clinically significant gram-negative bacteria as *Escherichia coli, Salmonella dublin, Salmonella typhose, Salmonella typhimurium, Shigella flexneri, Citrobacter freundii, Klebsialla pneumoniae, Vibrio cholerae, Vibrio anguillarum, Enterobacter aerogenes, Pasteurella multocida, Haemophilus influenzae, Yersinia enterocollitica, Pasteurella haemolytica, Proteus mirabilis* and *Proteus vulgaris,* the causative organisms of such ailments as travellers diarrhoea, urinary tract infections, shigellosis, typhoid fever and cholera in humans, as well as animal diseases such as calf neonatal enteritis, pig post-weaning enteritis and chicken colisepticeamia.

The compounds according to the invention have also been found to be effective in the treatment of prophylaxis of certain cardiovascular conditions such as thrombocytopaenia, particularly thrombocytopaenia purpura, which may be associated with AIDS. In particular, there is disclosed the use of 3'-azido-3'-dioxythymidine in treatment of idiopathic thrombocytopaenia purpura in a human by administering an effective treatment amount of said human.

The compounds according to the invention are hereinafter referred to broadly as 3'-azido-2',3'-dideoxy pyrimidine nucleosides, which term is used herein to include pyrimidine nucleoside analogues and derivatives (including salts and esters) which are essentially structurally based on a pyrimidine ring linked at the 1-position to a furanosyl ring.

Thus, in a first aspect of the present invention is provided pharmaceutically acceptable 3'-azido-2',3'-dideoxy pyrimidine nucleosides, for use in therapy.

In a second aspect is provided pharmaceutically acceptable 3'-azido-2',3'-dideoxy pyrimidine nucleosides for use in the treatment or prophylaxis of diseases as described above.

In a further aspect of the present invention is provided the use of pharmaceutically acceptable 3'-azido-2',3'-dideoxy pyrimidine nucleosides, particularly where the said nucleoside is a compound of formula (I), in the manufacture of a medication for the treatment of any of the above-mentioned diseases.

Preferred classes of nucleoside according to the invention are cytidine derivatives, e.g. compounds of formula (I) wherein $R^3$ is amino or alkylamino, wherein the 3' azido group is in the arythro configuration ("down azido"), thymidine derivatives (e.g. compound of formula (I) wherein $R^3$ is as defined other than amino or alkylamino and $R^4$ is as defined not including H) with the 3' azido in either the erythro or threo ("up azido") configuration, and nucleosides unsaturated between the 5C and 6C positions. alkylamino and $R^4$ is as defined not including H) with the 3' azido in either the erythro or threo ("up azido") configuration, and nucleosides unsaturated between the 5C and 6C positions.

With regard to the compounds of formula (I) above, the above-mentioned alkyl groups advantageously contain 1 to 8 carbon atoms, particularly 1 to 4 carbon atoms, e.g. methyl or ethyl groups. The above-mentioned aryl groups including the aryl moieties of such groups as aralkoxy are preferably phenyl groups optionally substituted by one or more appropriate substituents. The above-mentioned alkenyl and alkynyl groups advantageously contain 2 to 8, particularly 2 to 4, carbon atoms, e.g. ethenyl or ethynyl.

Further classes of preferred compounds of formula (I) include those wherein one or more of $R^1$, $R^2$, $R^3$ and $R^4$ are as defined below, namely $R^1$ is hydroxy, mercapto, $C_{1-4}$ alkoxy or amino;

$R^2$ is hydrogen, methyl or acyl;

$R^3$ is hydroxy or mercapto when a thymidine derivative (as defined above) or amino when a cytidine derivative (as defined above); and $R^4$ is hydrogen when a cytidine derivative or halogen or perhalomethyl when a thymidine derivative; and 5'-esters of such compounds including straight or branched chain alkyl esters optionally substituted with carboxy groups, e.g. succinate, $C_{1-6}$ thio esters, optionally substituted aryl esters, mesylate, glucuronide or mono-, di- or tri-phosphates.

The invention also provides the novel compounds of formula (I) above and their pharmaceutically acceptable derivatives. Thus, in an alternative aspect of the invention is provided the compounds of formula (I) provided that when $R^1$ and $R^3$ are each hydroxy, $R^2$ is hydrogen, $R^4$ is methyl, and (a) when $N_3$ is in the threo configuration, then $R^5$ is not hydroxy, and (b) when $N_3$ is in the erythro configuration then $R^5$ is not hydroxy, also excluding the acetate, mono- and tri-phosphates of such compound.

The 3'-azido-2',3'-dideoxy-pyrimidine nucleosides according to the invention may be prepared in conventional manner using techniques that are well known in the art, e.g. as described in Synthetic Procedures in Nucleic Acid Chemistry, 1, 321 (1968), T. A. Krenitsky et al., J. Med. Chem, 26, 981, (1983) and Nucleic Acid Chemistry, Improved and New Synthetic Processes, Methods and Techniques, Parts 1 and 2, Ed. L. D. Townsend, R. S. Tipson, (J. Wiley) 1978, which disclosures are herein incorporated by reference.

The present invention further includes a process for the preparation of compounds of formula (I) and pharmaceutically acceptable derivatives thereof which comprises (A) reacting a compound of formula:

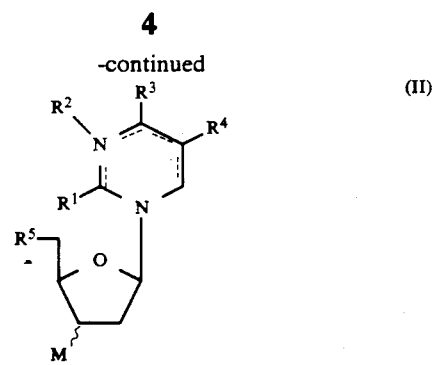

(wherein $R^1$, $R^2$, $R^3$, $R^4$ and $R^5$ are as defined above and M represents a precursor group for the 3'-azido group) or a derivative (e.g. an ester or salt) thereof, with an agent or under conditions serving to convert the said precursor group into the desired azido group;

(B) reacting a compound of formula

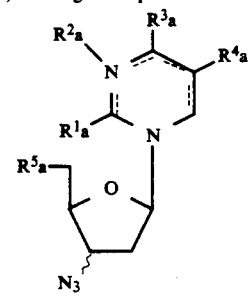

(wherein $R_a^1$, $R_a^2$, $R_a^3$ $R_a^4$ and $R_a^5$ respectively represent the groups $R^1$, $R^2$, $R^3$, $R^4$ and $R^5$ or precursor groups therefor, providing that at least one of $R_a^1$, $R_a^2$, $R_a^3$, $R_a^4$ and $R_a^5$ represents a precursor group) with an agent or under conditions serving to convert the said precursor group(s) into the corresponding desired groups; or (C) reacting a compound of formula

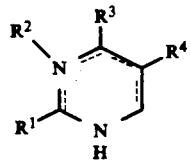

(wherein $R^1$, $R^2$, $R^3$ and $R^4$, are as defined above) or a functional equivalent thereof, with a compound serving to introduce the desired ribofuranosyl ring at the 1-position of the compound of formula (IV); and thereafter, or simultaneously therewith, effecting one or more of the following optional conversions:

(i) when a compound of formula (I) is formed, converting the said compound into a pharmaceutically acceptable salt or ester thereof, (ii) when a pharmaceutically acceptable salt or ester of formula (I) is formed, converting the said salt or ester into the parent compound of formula (I).

In the above-described process according to the invention, it will be appreciated that the choice of the precursor compounds of formulae (II) and (III) will be dictated largely by the particular compound of formula (I) that it is desired to prepare, the above-mentioned agents and conditions being selected accordingly from those that are known in the art of nucleoside synthetic chemistry. Examples of such conversion procedures are described hereinafter for guidance and it will be understood that they can be modified in conventional manner depending on the desired compound of formula (I). In particular, for example, where a conversion is described which would otherwise result in the undesired reaction of labile groups then such groups may be protected in conventional manner, with subsequent removal of the protecting groups after completion of the conversion.

Thus, for example, with regard to process (A) the group M in the compound of formula (II) may represent, for example, a halogen (e.g. chlorine), hydroxy or organusulphonyloxy e.g. trifhloromethylsulphonyloxy, methanesulphonyloxy or p-toluene sulphonyloxy radical. For the preparation of compounds of formula (I) in which the 3'-azido group is in the threo configuration, a compound of formula (II) in which the group M is a hydroxy group in the erythro configuration (in which the 5'-hydroxy group is advantageously protected, e.g. with a trityl group) may be treated for example with tryphenylphosphine, carbon tetrabromide and lithium azide. Alternatively, M may represent an anganosulphonyloxy leaving group in the threo configuration which may be converted into an azido group in the threo configuration by treatment for example with lithium or sodium azide, the 5'-hydroxy group being similarly protected as described above. Removal of the 5'-trityl protecting group may be subsequently effected, e.g. by treatment under mild acidic conditions or zinc bromide.

For the preparation of compounds of formula (I) in which the 3'-azido group is in erythro configuration, a compound of formula (II) in which the group M is a halogen (e.g. chloro) group in the threo configuration (in which the 3'-hydroxy is advantageously protected, e.g. with a trityl group) may be treated for example with lithium or sodium azide. The 3-threo-halogen (e.g. chlorine) starting material may be obtained for example by reaction of the corresponding 3-erythro-hydroxy compound with for example triphenylphosphine and carbon tetrachloride, or alternatively by treatment with organosulphonyl halide (e.g. trifluoromethanesulphonyl chloride) to form a corresponding 3-erythro-organosulphonyloxy compound which is then halogenated, e.g. as described above. Alternatively a 3-threo-hydroxy or organosulphonyloxy compound of formula (II) may be treated, for example with triphenylphosphone, carbon tetrabromide and lithium azide to form the corresponding 3-erythro azido compound. Removal of any protecting group may then subsequently be effected, e.g. as above. With regard to process (B) the following represent examples of various procedures by which the precursor groups may be converted into the desired $R^1$, $R^2$, $R^3$ and $R^4$ groups:

a) When $R^1$ represents an alkoxy (e.g. methoxy or ethoxy) group, such compounds may be prepared from corresponding compounds of formula (III) in which $R_a^1$ represents a hydroxy, e.g. by treatment with an appropriate alkylating agent, e.g. an alkanol, conveniently in the presence of potassium carbonate;

b) When $R^1$ represents a mercapto group, such compounds may be prepared from corresponding compounds of formula (III) in which $R_a^1$ represents an alkoxy (e.g. ethoxy) group, e.g. by treatment with hydrogen sulphide;

c) When $R^2$ represents an alkyl group, such compounds may be prepared from corresponding compounds of formula (III) in which $R_a^2$ represents a hydrogen atom, e.g. by treatment with an alkylating agent, e.g. N,N-dimethylformamide dimethylacetal;

d) When $R^3$ represents a mercapto group, such compounds may be prepared from corresponding compounds of formula (III) in which $R_a^3$ represents an appropriate leaving group, e.g. 1,2,4-triazolyl, by treatment for example with an alkali metal (e.g. sodium) mercaptan;

e) When $R^3$ represents an amino group, such compounds may be prepared from corresponding compounds of formula (III) in which $R_a^3$ represents a hydroxy group by treating with an aminating agent, e.g. ammonium sulphate, in a bomb;

f) When $R^4$ represents a halo (e.g. chloro) radical, such compounds may be prepared from corresponding compounds of formula (III) in which $R_a^4$ represents a hydrogen atom by treatment with a halogenating agent e.g. m-chloroperbenzoic acid.

With regard to process (C), this may be effected for example by treating the appropriate pyrimidine of formula (IV) or a salt or protected derivative thereof, with a compound of formula.

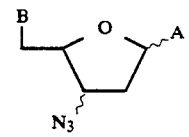

(wherein A represents a leaving group, e.g. an acetoxy or benzocyloxy or halo, e.g. chloro group and B represents an optionally protected hydroxy group e.g. a p-tolueresulphonyloxy group, and subsequently removing any protecting groups.

The compounds of formula (I) wherein $R^5$ is hydroxy and the azido group is in either configuration may also be prepared in conventional manner for example as described in the following references or by methods analogous thereto, J. R. Horwitz et al., J. Org. Chem. 29, (Jul. 1964) 2076–78, and M. Imazawa et al., J. Org. Chem., 43 (15) (1978) 3044–3048; K. A. Watanabe et al., J. Org. Chem., 45, 3274 (1980); or R. P. Glinski et al., J. Chem. Soc. Chem. Commun., 915 (1970).

Where a compound of formula (I) is formed, such a compound may be converted into a pharmaceutically acceptable, phosphate or other ester by reacting the compound of formula (I) with respectively a phosphorylating agent, e.g., POCl₃ or an appropriate esterifying agent, e.g. an acid halide or anhydride. The compounds of formula (I) including esters thereof may be converted into pharmaceutically acceptable salts thereof in conventional manner, e.g. by treatment with an appropriate base.

Where an ester or salt of a compound of formula (I) is formed, such a compound may be converted into the parent compound, e.g. by hydrolysis.

A pharmaceutically acceptable 3'-azido-2',3'-dideoxy pyrimidine nucleoside (hereafter referred to as the active ingredient) may be administered by any suitable route including oral, rectal, nasal, topical (including buccal and sublingual), vaginal and parenteral (including subcutaneous, intramuscular, intravenous and intradermal). It will be appreciated that the preferred route may vary with, for example, the condition and age of the recipient.

In general, for each of the above-mentioned viral infections, a suitable effective dose will be in the range 1.0 to 250 mg per kilogram body weight of recipient per day, preferably in the range of 1 to 100 mg per kilogram body weight per day and most preferably in the range 5 to 40 mg per kilogram body weight per day. The desired dose is preferably presented as two, three, four, five, six or more sub-doses administered at appropriate intervals throughout the day. These sub-doses may be administered in unit dosage forms, for example, containing 10 to 1000 mg. preferably 50 to 500 mg and most preferably 100 to 400 mg of active ingredient per unit dosage form.

Clinical trials with 3'-azido-3'-deoxythymidine have established that a suitable regimen for treating thrombocytopaenia is about 5.0 mg/kg every 4 hours administered either orally or intravenously.

A preferred dose is administered to achieve peak plasma concentrations of the said nucleoside of from about 1 to about 100 $\mu M$, preferably about 2 to 80 $\mu M$, most preferably about 3 to about 50 $\mu M$. This may be achieved, for example, by the intraveneous injection of a 0.1 to 5% solution of the active ingredient in saline as a bolus containing about 1 to about 40 mg/kg of the active ingredient. Desirable blood levels may be maintained by a continuous infusion to provide about 0.01 to about 0.4 mg/kg/hour or by intermittent infusions containing about 0.4 to about 10 mg/kg of the active ingredient.

While it is possible for the active ingredient to be administered alone it is preferable to present it as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual, vaginal or parenteral (including subcutaneous, intramuscular, intravenous and intradermal) administration. The formulations may conveniently be presented in unit dosage form and may be prepared by any methods well known in the part of pharmacy.

Such methods include the step of bringing into association the active ingredient with the carrier which constitutes one or more accessory ingredients. In general, the formulations are prepared by uniformly and intimately bringing into association the active ingredient with liquid carriers of finely divided solid carries or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A table may be made by compression or molding, optionally with one or more accessory ingredients. Compressed tablets may be prepared by compressing in a suitable machine the active ingredient in a free-flowing form such as a powder or granules, optionally mixed with a binder, lubricant, insert diluent, preservative, surface-active or dispersing agent. Moulded tablets may be made by moulding in a suitable machine or mixture of the powdered compound moistened with an inert liquid diluent. The tablets may optionally be coated or scored and may be formulated so as to provide slow or controlled release of the active ingredient therein.

Formulations suitable for topical administration in the mouth include lozenges comprising the active ingredient in a flavoured basis, usually sucrose and acacia or tragacanth, pastilles comprising the active ingredient in an inert basis such as gelatin and glycerin, or sucrose acacia; and mouthwashes comprising the active ingredient in a suitable liquid carrier.

If desired, the active ingredient may be presented in a topical ointment or cream containing the active ingredient in an amount of for example 0.075 to 20% w/w, preferably 0.2 to 15% w/w, and most preferably 0.5 to 10%. When formulated in an ointment, the active ingredients may be employed with either a paraffinic or a water-miscible ointment base. Alternatively, the active ingredients may be formulated with an oil-in-water cream base. Other topical formulations include dermal patches.

Formulations for rectal administration may be presented as a suppository with a suitable base comprising for example cocoa butter or a salicylate.

Formulations suitable for nasal administration wherein the carrier is a solid include a coarse powder having a particle size, for example, in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient and aqueous and non aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include flavouring agents.

It should be appreciated that the said 3'-azido-3'-deoxynucleosides may be administered singly or in conjunction with other therapeutic agents. For example, one possible opportunistic infection frequently observed in suffers of AIDS is herpetic meningitis. The nucleoside according to the invention may then be administered for the treatment of AIDS in conjunction with, for example, 9-(2-hydroxyethoxymethyl) guanine (acyclovir) or 2-amino-9-(2-hydroxyethoxymethyl) guanine for the treatment of meningitis.

Thus, in a further aspect of the present invention is provided 3-azido-2',3'-dideoxypyrimidine nucleosides in conjunction with another therapeutic agent in therapy.

The following Examples illustrate pharmaceutical formulations and 3'-azido-2',3'-dideoxy-pyrimidine nucleosides according to the invention.

EXAMPLE 1

Tablet

| | |
|---|---|
| Active ingredient | 100 mg |
| Lactose | 200 mg |
| Starch | 50 mg |
| Polyvinylpyrrolidone | 5 mg |
| Magensium stearate | 4 mg |
| | 359 mg |

Tablets were prepared from the foregoing ingredients by wet granulation followed by compression.

EXAMPLE 2

Injectable

| | |
|---|---|
| Active Ingredient | 0.125 |
| Sterile, pyrogen-free, pH 7 phosphate buffer, q.s. to | 25 ml |
| 3'Azido-3'-Deoxy-5'-O-succinylthymidine | |
| 3'-Azido-3'-Deoxy-5'-O-mesylthymidine | |
| 3'-Azido-5'-O-(4-methyl-benzoyl)-3'-deoxythmidine | |
| 5'-O-Acetyl-3'-azido-3'-deoxythymidine | cal. C-46.60 H-4.89 N-22.65 fnd. C-46.67 H-4.94 N-22.59 |
| 3'Azido-5'-O-(3-chloro-benzoyl)-3'-deoxythymidine | cal. C-50.31 H-3.97 N-17.26 Cl-8.74 fnd. C-50.16 H-4.03 N-17.13 Cl-8.66 |
| 3'-Azido-3'-Deoxy-5'-O-palmitoylthymidine | cal. C-61.67 H-8.57 N-13.85 fnd. C-61.85 H-8.59 N-13.75 |

EXAMPLE 6

Preparation of 1-(3-Azido-2,3-Dideoxy-β-D-Threo-Pentofuranosyl)-Thymine5'-Monophosphate Disodium Salt 200 mg (0.75 mmoles) of 1-(3-azido-2,3'-dideoxy-β-D-threo-pentofuranosyl)thymine (J. Org. Chem. (1980) 45, 3274–3278) were dissolved in 5 mL of triethylphosphate and chilled to −8° C. 274 μl (3 mmoles, 4 eq.) of phosphorus oxychloride was added all at once. TLC (n-PrOH:H2O:conc. NH4OH,7:1:3 on cellulose) indicated product formation but incomplete reaction after 3 hours. The reaction was stored in a −5° C. freezer overnight. The next morning the tic indicated 80–90% complete reaction. The reaction was poured onto 15–20 mL of ice water and the pH was adjusted to 7. The aqueous solution was extracted with chloroform (2×) and ether (2×). The traces of organic solvents were removed by gentle stripping on a rota-vap.

Freshly prepared deactivated charcoal was added to the aqueous solution until UV assay indicated 90% of the nucleotide had been absorbed. The mixture was filtered and washed with water until no UV absorption was found in the filtrate. The compound was washed off the charcoal by slurrying in 50% aqueous ethanol containing 2% conc. NH4OH and filtering. The wash was repeated a second time. The ethanol and NH4OH were removed by evaporation. The pH was adjusted to 7. The solution was passed through 10 mL of DOW 50 (Na+) to obtain the compound as the disodium salt. The solution was freeze dried. The title compound (104 mg) was obtained as a solid which was one peak by HPLC. NMR H δ7.77 (d,J6,5±1.2Hz 6H) 66.18(dd,J1',2a'-3,0Hz,J1',2b'=7.7Hz 1'H) δ4.64–4.45(m,3'H) δ4.45–4.28 (m, 4'H) 4.28–4.08(m,5'H) δ3.06–2.70(m-,2a'H) δ2.50–2.24(m,2b'H) δ1.95(d,J5,6=1.2Hz,5CH3) NMR 31p δ2.33 (JPH=6.3)

EXAMPLE 7

Sodium Salt of 3'-Azidothymidine

Approximately one gram of 3'-azidothymidine as prepared by the method of Example 6 was dissolved in 50 mL of distilled water. The pH was adjusted to 12 with 1N NaOH. Approximately half of the solution was freeze dried. A white powder, 0.415 g, resulted. Elemental analysis indicated the formation of a full sodium salt.

EXAMPLE 8

5'-Phosphate of 3'-Azidothymidine

The 5'-phosphate of 3'-azidothymidine was prepared by the method of R. P. Glinski, M. S. Khan, R. L. Kalamas and C. L. Stevens, J. Chem. Soc. Chem. Commun., 915 (1970).

EXAMPLE 9

1-(3'-Azido-2',3'-Dideoxy-β-D-Threo-Pentofuranosyl)Thymine 1-(3'-azido-2',3'-dideoxy-β-D-threo-pentofuranosyl)thymine was prepared by the method of A. Matsuda, K. A. Watanabe and J. J. Fox, J. Org. Chem., 45, 3274 (1980).

EXAMPLE 10

(a) 2,5'-anhydro-3'-Azido-3'-Deoxythymidine 2,5'-Anhydro-3'-azido-3' deoxythmidine was prepared from 3'-azidothymidine by a two step reaction sequence.

The 5'-hydroxyl of 3' azidothymidine (3.0 g, 11.2 mMol) was mesylated by the addition of methanesulphonyl chloride (2.7 mL) to a solution of the starting material in dry pyridine (20 mL). The reaction was allowed to proceed at 5° C. for one hour, then poured onto ice water. The precipitate was collected by filtration. The desired product was obtained by reacting the 3'-azido-4'-mesylthymidine obtained from the first step with potassium carbonate (0.78 g, 5.6 mMol) in DMF (75 mL). The reaction was heated in an 80° C. oil bath for six hours, then poured into ice water. The product was extracted from the water with ethyl acetate. The solvent was removed in vacuo and the resultant oil was flash chromatographed on silica gel by elution with CHCl3:MeOH (9:1 v/v). The product was obtained in low yield.

mp=184°–186° C.

(b)

3'-Azido-3',5'-Dideoxy-5'-[(N,N-Dimethylthiocarbamoyl)Thio]Thymidine

The sodium salt of dimethyldithiocarbamic acid dihydrate (0.642 g, 3.58 mMol) and 3.58 mL of a solution of 1N tetrabutylammonium hydroxide in MeOH was added to 25 mL of DMF. The solution was boiled to remove water and MeOH. After cooling, 5',2-anhydro-3'-azidothymidine (0.85 g, 3.4 mMol) dissolved in 15 mL of DMF was added. The reaction was heated in a 55° C. oil bath overnight. The reaction was poured onto ice water and a precipitate was removed by filtration. The product was extracted from the filtrate with ethyl acetate. The ethyl acetate was removed in vacuo and the resulting oil was purified by flash chromatography on silica gel by elution with $CHCl_3$:MeOH (95:5 v/v). Chromatography was required a second time on silica gel. The second elution was with $CHCl_3$:MeOH (98:2 v/v). Final purification was accomplished by reverse phase chromatography on $C_{18}$ eluted with water:methanol (3:7). The yield was 2.5%.

EXAMPLE 11

3'-Azido-5'-O-Acetyl-4-Thiothymidine

3'-Azido-5'-O-acetyl-4-(1,2,4-triazole)thymidine (Lin, et al., J. Med. Chem. 26, 1691 (1983)) (1.41 g; 3.9 mMol) was dissolved in 100 mL acetone and 30 mL $H_2O$, then treated with 0.39 g $NaSH.xH_2O$ (Sung, J. Chem. Soc. Chem. Comm. 522, (1982)). The mixture was stirred for 30 min, the volume reduced by ¼ and extracted with 200 mL $CHCl_3$. The $CHCl_3$ was washed with 100 mL $H_2O$ and dried over $Na_2SO_4$. The solvent was removed in vacuo and the resultant oil placed on a silica gel pad (6.5×3 cm) followed by elution with 750 mL $CHCl_3$. The solvent was removed in vacuo to yield a yellow oil which was recrystallized from I-PrOH to yield 0.64 g (1.9 mMol; 48.7%).

mp=75°-78° C.

EXAMPLE 12

3'-Azido-4-Thiothymidine

3'-Azido-5'-O-acetyl-4-thiothymidine (0.25 g; 0.76 mMol, Example 11) was dissolved in a mixture of 5 mL of dioxane and 5 mL of conc. $NH_4OH$ and stirred for 18 hrs. The solvent was removed in vacuo and the residue applied to a silica gel column followed by elution with $CHCl_3$/EtOAc (3:1 v/v). The appropriate fractions were combined and the solvent removed in vacuo to yield a yellow oil which was dissolved in $Et_2O$, forming crystals upon concentration: 0.16 g (0.56 mMol; 74%). m.p.=116°-118° C.

EXAMPLE 13

3-N-Methyl-3'-Azidothymidine

3'-Azidothymidine (0.5 g; 1.9 mMol) and N,N-dimethylformamide dimethylacetal (Zemlicksa, Coll. Czech. Chem. Comm. 35, 3572 (1972)) (0.9 mL; 7.5 mMol) were refluxed to 20 mL $CHCl_3$ for 48 hours. The solvent was removed in vacuo and the material placed on a silica column. Elution with EtOAc/$CHCl_3$ (1:1 v/v) resulted in pure material as a viscous oil: 0.26 g (0.9 mMol, 47%).

EXAMPLE 14

3'-Azido-2-Thiothymidine

The synthesis of 3'-Azido-2-thiothymidine was accomplished by a five step reaction sequence starting from 3',2-O-anhydro-5'-tritylthymidine (J. J. Fox, J. Org. Chem, 28, 936, (1963)).

3'2-O-Anhydro-5'-tritylthymidine (10.5 g, 22.4 mMol) was added to a solution of sodium (0.52 g, 22.4 mMol) in dry ethanol (1.2 L) and the reaction was refluxed for six hours. The reaction was cooled and neutralized with 1N HCl. The solvent was removed in vacuo and the resultant all purified by flash chromatography on silica gel by elution with $CHCl_3$:MeOH (96.4 v/v). A 30% yield of 1-(2'-deoxy-5'-trityl-D-lyxofuranosyl)-2-ethoxythymine was obtained. The 2-ethoxythymidine derivative (3.5 g, 16.8 mMol) was dissolved in 35 mL of DMF containing 2.2 mL of triethylamine. The cold solution was saturated with $H_2S$. The reaction was placed in a steel bomb and heated at 95° C. After twenty seven hours TLC indicated no starting material remained. The reaction was purged with $N_2$ for several hours and poured onto ice water. The product was collected by filtration and purified by flash chromatography on silica gel by elution with $CHCl_2$:MeOH (97:3 v/v). A 37% yield of 1-(2'-deoxy-5'-trityl-β-D-lyxofuranosyl)-2-thiothymine was obtained. The UV max at pH1 of 277 nm and at pH11 of 241 nm indicated the formation of a 2-thiothymidine. The 3'-hydroxyl of the thiothymidine derivative was mesylated as follows: methanesulfonyl chloride (665 μL, 3.5 eq.) was added in four portions over six hours to a solution of 1-(2'-deoxy-5'-trityl-β-D-lyxofuranosyl)-2-thiothymidine (1.25 g) in dry pyridine (15 mL) at 5° C. The reaction was maintained at 5° C. overnight. The reaction was poured onto ice water and the product collected by filtration. Purification was accomplished by flash chromatography on silica gel by elution with ethyl acetate:hexane (1:1 v/v). The yield was 30%. Lithium azide (0.3 g, 6 mMol) was dissolved in 20 mL of dry DMF and 1-(2'-deoxy-3'-mesyl-5'-trityl-β-D-lyxofuranosyl)-2-thiothymine (0.72 g, 1.2 mMol) was added. The DMF solution was heated at 85° C. for 2.5 hours. The reaction was poured onto ice water and the product collected by filtration. Purification was accomplished by flash chromatography on silica gel by elution with $CHCl_3$:MeOH (98:2 v/v). The yield was 78%. A band in the IR at 2100 $CM^{-1}$ indicated the presence of an alkyl azide. The UV confirmed the presence of a 2-thiothymidine. The final product was prepared by deblocking the 5'-hydroxyl of 3'-azido-2-thio-5'-tritylthymidine (0.1 g) in 80% acetic (5 mL) on a steambath for fortyfive minutes. 3'-Azido-2-thiothymidine (0.021 g) was obtained by chromatography on silica gel by elution with $CHCl_3$:MeOH (96:4 v/v) in 37% yield.

EXAMPLE 15

3'-Azido-2-Ethoxythymidine

3'-Azido-2-ethoxythymidine was prepared by refluxing 3'-azido-5'-mesylthymidine (2.6 g, 7.3 mMol) in dry ethanol (25 mL) with two equivalents of potassium carbonate (1.08 g, 7.5 mMol) for five hours. The solution was neutralized and taken to an all in vacuo. The oil was purified by flash chromatography on silica gel by elution with ethyl acetate:methanol. The desired product was isolated in 39% yield.

mp=98°-100° C.

EXAMPLE 16

3'-Azido-2-Methoxythymidine

3'-Azido-2-methoxythymidine was prepared from 3'-azido-5'-mesylthymidine (1.6 g, 4.6 mMol) by the procedure of Example 15. The yield was 42%.
mp=47°-51° C.

EXAMPLE 17

3'-Azido-2'-Deoxy-5-Methylisocytidine 2,5'-Anhydro-3'-azido-3'-deoxythymidine (0.35 g; 1.4 mMol) was dissolved in 15 mL of MeOH presaturated with ammonia and placed in a bomb at 77° C. (oil bath) for 48 hours (Skaric and Matulic-Adamic, Helv. Chim. Acta. 63, 2179 (1980)). By TLC (6:1 v/v $CHCl_3$/MeOH) the reaction was incomplete. The solvent was removed in vacuo and the resultant oil placed on a silica gel column followed by elution with $CHCl_3$/MeOH (6:1 v/v). The appropriate fractions were combined to yield 0.14 g (0.53 mMol; 38%).
mp=107°-108° C.

EXAMPLE 18

5-Chloro-3'-Azido-2'-Deoxyuridine

3'-Azido-2'-deoxyuridine (0.25 g; 1 mMol) was dissolved in 2 mL dry dimethylacetamide (DMAC), cooled to 0° C. and 2 mL of 0.5 m HCl in DMAC was added . m-Chloroperbenzoic acid (0.277 g; 1.6 mMol) was added in two portions over ten minute and the mixture was allowed to come to ambient temperature. After two hours, 4 mL $H_2O$ was added and the solution filtered. The aqueous DMAC solution was extracted with $Et_2O$ (3×3 mL) and the $Et_2O$ was evaporated in vacuo to an oil which was applied to a silica gel column. Elution with $CHCl_3$/MeOH (15:1 v/v), combination of appropriate fractions and evaporation in vacuo yielded an oil which was crystallized from $Et_2O$. Yield 58.5 (0.2 mMol, 20%).
mp=169°-170° C.

EXAMPLE 19

3'-Azido-5-Bromo-2'-Deoxyuridine

3'-Azido-5-bromo-2'-doxyuridine was prepared from the known 3'-azido-2'-deoxyuridine (T. A. Krenitsky, et al., J. Med. Chem., 26, 891, (1983)) (0.827 g, 3.3 mMol) by first acetylating the 5'-hydroxyl with acetic anhydride (15 mL) then by brominating the 5 position by the addition of acetic acid (0.5 mL) and bromine (0.566 g). The red-brown solution was stirred at room temperature for two hours. The reaction was taken to an oil in vacuo and triturated with ethyl ether. The oil was dissolved in methanol ammonia to remove the acetyl group. The desired product was isolated by chromatography on silica gel by elution with $CHCl_3$:MeOH (95:5 v/v). The yield as 32%.
mp=148°-149° C.

EXAMPLE 20

3'-Azido-2'-Deoxy-5-Iodouridine

3'-Azido-2'-deoxy-5-iodouridine was prepared from 2'-deoxy-5-iodouridine (10 g, 28 mmol) by a four step reaction sequence described in the literature (T. A. Krenitsky, et al., J. Med. Chem, 26, 891, (1983)).
mp=126°-130° C.

EXAMPLE 21

3'-Azido-2'-Deoxy-5-Trifluoromethyluridine

3'-Azido-2'-deoxy-5-trifluoromethyluridine was prepared by a four step reaction sequence.

The 5'-hydroxyl of 2'-deoxy-5-trifluoromethyluridine (3.0 g, 16.9 mMol) was tritylated by the addition of triphenylmethyl chloride (5.65 g, 20.3 mMol) to the starting material in a suspension of dichloromethane (1.4 L ml), pyridine (70 mL), an 3 A molecular sieves (55 g). The reaction was stirred at room temperature for four days. After filtration and evaporation in vacuo, the oily product was chromatgraphed on silica gel by elution with $CH_2Cl_2$:MeOH (95:5 v/v). The product fractions were combined and the solvent removed in vacuo. The resulting oil was triturated with water and the solid that formed was collected by filtration. The 3'-hydroxyl was chlorinated by dissolving the 5'-protected uridine (3.0 g) in dimethylacetamide (30 mL) containing triphenylphosphine (3.27 g) and adding carbon tetrachloride (51 mL). The reaction was stirred at room temperature overnight. One milliliter of methanol was added. The reaction was taken to an oil and chromatographed on silica gel by elution with $CH_2Cl_2$:EtOAc (9:1 v/v). The desired product was collected as an oil. The oil, 1-(3-chloro-2'-deoxy-5'-trityl-threo-β-D-ribofuranosyl)-5-trifluoromethyluracil, was deblocked by dissolving in nitromethane (80 mL) and adding zinc bromide (4.45 g) dissolved in nitromethane (80 mL) by the method of V. Kohil, et al., Tetrahedron Letters, 21, p 2683, 1980. The reaction was stirred at room temperature overnight. More zinc bromide (3.0 g) was added the next day and the reaction was allowed to go overnight. A final addition of zinc bromide (3.7 g) with gentle heating pushed the reaction to a stopping point. The reaction was poured into 1M ammonium acetate. The produce was extracted into dichloromethane. The dichloromethane was removed in vacuo and the resulting oil was chromatographed on silica gel by elution with $CH_2Cl_2$:MeOH (95:5 v/v). The final product was obtained by treating 1-(3-chloro-2-deoxy-β-D-ribofuranosyl)-5-trifluoromethyluracil (0.48 g, 1.53 mMol) with lithium azide (0.19 g, 3.8 mMol) in dimethylacetamide (4.8 mL). The reaction was heated at 90° C. for four hours. The reaction was taken to an oil and chromatographed on silica gel by elution with $CHCl_3$:MeOH (95:5 v/v). Chromatography was required a second time. Elution on silica gel with $CH_2Cl_2$:MeOH (97:3 v/v) resulted in a nearly pure product. Crystallization from toluene produced the pure produce in 10% yield.

EXAMPLE 22

3'-Azido-2'-Deoxycytidine

3'-Azido-2'-deoxycytidine was prepared from 3'-azido-2'-deoxyuridine (2.2 g, 7.9 mMol) as the HCl salt by the procedure of T. A. Krenitsky, et al., J. Med. Chem., 26, 891, (1983). The yield was 40%.
mp=174.5°-176.5° C.

EXAMPLE 23

3'-Azido-2'-Deoxy-5-Methylcytidine

3'-Azido-2'-deoxy-5-methylcytidine was prepared from 3' azidothymidine (0.8 g, 3.0 mMol) by the procedure of Example 22. The yield was 19%.

EXAMPLE 24

Threo-3'-Azido-2'-Deoxycytidine

The synthesis of threo-3'-azido-2'-deoxyctidine was accomplished from 2'-deoxyuridine in four steps.

The 5'-hydroxyl of 2'-deoxyuridine was tritylated by the method described in Synthetic Procedures in Nucleic Acid Chemistry, 1, 321, (1968).

Threo-3'-Azido-2'-deoxy-5'-trityluridine was prepared by reacting 2'-deoxy-5'-trityluridine (5.0 g, 10.6 mMol) with triphenylphosphine (3.07 g, 11.7 mMoles, 1.1 sq.) and carbon tetrabromide (3.88 g, 11.7 mMol, 1.1 eq.) and lithium azide (5.21 g, 106 mMol, 10 q.) In DMF (80 mL). The carbon tetrabromide was added last. The reaction was allowed to go at room temperature overnight. Methanol (5 mL) was added. The solution was taken to an oil in vacuo and flash chromatographed on silica gel by elution with ethyl acetate. Deblocking the 5'-hydroxyl was accomplished by heating in 80% acetic acid on a steambath for twenty minutes. Upon cooling, the tritylcarbinol precipitated and was filtered off. The filtrate was taken to dryness and slurried in ethyl ether. The product, threo-3'-azido-2'-deoxyuridine, was carried on without further purification. The final product, threo-3'-azido-2'-deoxycytidine as the HCl salt, was prepared from the uridine analogue by exactly the same procedure as used for the preparation of the erythro isomer (T. A. Krenitsky, et al., J. Med. Chem., 26, 891, (1983)). The yield was 0.021 g, 7%.

EXAMPLE 25

3'-Azido-3'-Deoxythymidine a) 2,3'-Anhydrothymidine

Thymidine (85.4 g: 0.353 mol) was dissolved in 500 ml dry DMF and added to N-(2-chloro-1,1,2-trifluoroethyl) diethylamine (100.3 g: 0.529 mol) (prepared according to the method of D. E. Ayer, J. Med. Chem. 6, 608 (1963). This solution was heated at 70° C. for 30 minutes them poured into 950 ml ethanol (EtOH) with vigorous stirring. The product precipitated from this solution was filtered. The EtOH supernatant was refrigerated then filtered to yield a total of 47.75 g (0.213 mol. 60.3%) mp=228°-230° c.

b) 3'-Azido-3'-Deoxythymidine 2,3'-Anhydrothymidine (25 O: 0.1115 mol) and NaN$_3$ (29 g, 0.446 mol) was suspended in a mixture of 250 ml DMF and 38 ml H$_2$O. The reaction was refluxed for 5 hours at which time it was poured into 1 liter of H$_2$O. The aqueous solution was extracted with EtOAc (3×700 ml). The EtOAc was dried over Na$_2$SO$_4$, filtered and the EtOAoac was removed in vacuo to yield a viscous oil. This oil was stirred with 200 ml water resulting in a solid 9.15 g (0.0342 mol, 30.7%). mp=116°-118° C.

EXAMPLE 26

Triphosphate of 3'-Azido-3'-Deoxthymidine

The triphosphate of 3'-azido-3'-deoxythymidine was prepared from the 5'-monophosphate of 3'-azido-3'-deoxythymidine in four stages:

(a) Bia (nBu)$_3$N Pyrophosphate

A column of DOW 50 pyridinium resin was prepared by pouring 40 mL of resin into a 25 cm diameter column and washed with water until no more colour eluted. Pyrophosphate decahydrate (1.12 g, 2.51 mM) was dissolved in 30 mL of water and applied to the column. The column was eluted with water. A 125 mL fraction of the eluant which contained UV absorbing material was collected. The volume was reduced to 10 mL in vacuo and tri-n-butyl amine (1.2 mL) was added. The volume was reduced in vacuo and the residue was dried by coevaporation with pyridine four times. The product was stored in a freezer (−5° C.).

(b) Hydrogen Form of the Monophosphate of 3'-Azido-3'-Deoxythymidine

The hydrogen form of the monophosphate was prepared by passing the ammonium salt (0.1 g, 0.283 mMol) dissolved in 6 mL of water, through a 1.5 mL (10 eq.) column of DOW 50 H+.

(c) Phosphormorpholidate Derivative of 3'-Azido-3'-Deoxythymidine

In 9 mL of water was dissolved 0.283 mMol of the hydrogen form of the monophosphate obtained in stage b). Morpholine (99 µL, 1.13 mMol, 4 eq.) was added and the solution heated to reflux. Dicyclohexyl carbodiimide (0.234 g, 1.13 mMol, 4 eq.) dissolved in t-butanol (5 mL) was added over a three hour period. The reaction was refluxed overnight. The reaction was cooled to room temperature, filtered, and the solvents removed in vacuo. Ethanol was added and evaporated in vacuo four times. The residue was dissolved in methanol and the phosphormorpholidate precipitated by the addition of ether. The precipitate was triturated with ether four times and dried on a rotary evaporator. A weight yield of 97 mg, 50%, was noted.

(d) 3'-Azido-3'-Deoxythymidine-5'-Triphosphate

The phosphormorpholidate derivative obtained in stage c), was dried by a removal of pyridine in vacuo four times. The bis (n-Bu)$_3$N pyrophosphate obtained in stage a) was also dried by removal of pyridine in vacuo. The phosphormorpholidate was dissolved in pyridine, 5 mL, and added to the vessel containing the pyrophosphate reagent. The reaction was allowed to continue overnight at room temperature. The pyridine was removed in vacuo. Water was added to the residue and removed in vacuo three times. The residue was frozen.

EXAMPLE 27

Anti-HTLVIII Activity of 3'-Azido-3'-Deoxypyrimidine Nucleosides

Compounds of formula (I) were tested in vitro against HTLVIII and were found to have ED$_{50}$ values as shown in table 1.

TABLE 1

| Compound | ED$_{50}$(µM) |
| --- | --- |
| 3'-Azido-2',3'-dideoxythymidine | 0.005 |
| 3'-Azido-2',3'-dideoxythymidine-5'-phosphate | 50 |
| 1-(3'-Azido-2',3'-dideoxy-θ-D-threo-pentofuranosyl)thymine | 0.5 |
| 3'-Azido-2',3'-dideoxy-5-bromothymidine | 0.5 |
| 3'-Azido-2',3'-dideoxycytidine | 0.5 |

EXAMPLE 28

Anti-Thrombocytopaenia Activity of 3'-Azido-3'-deoxythymidine

A patient diagnosed as having thrombocytopaenia purpura (platelet count <100,000 mm−3) was treated for 6 weeks with 5 mg/kg of the title compound intravenously every 6 hours. Treatment was then changed to 5 mg/kg/4 hours orally for 4 weeks, discontinued for 2 weeks, recommenced at 5 mg/kg/4 hours orally of 5 weeks and then reduced to 2.5 mg/kg/4 hours orally for a further 7 weeks. Results are shown in FIG. 1.

Platelet count responds well to initial treatment, falls off with discontinuation of treatment and picks up with renewed therapy. From the final drop in numbers, therapy appears most effective above 2.5 mg/kg/4 hours.

EXAMPLE 29

Toxicity Assay

3'-Azido-2',3'-dideoxythymidine was administered to both mice and rats. The $LD_{50}$ value was found to be in excess of 750 mg/kg in both.

EXAMPLE 30

3'-Azido-5-Chloro-2',3'-Dideoxyuridine

3'-Azido-2'-deoxyuridine (0.25 g; 1 mMol) was dissolved in 2 mL dry dimethylacetamide (DMAC), cooled to 0° and 2 mL of 0.5M HCl in DMAC was added. m-Chloroperbenzoic acid (0.277 g; 1.6 mMol) was added in two portions over ten minutes and the mixture was allowed to come to ambient temperature. After two hours, 4 mL $H_2O$ was added and the solution filtered. The aqueous DMAC solution was extracted with $Et_2O$ (3×3 mL) and the $Et_2O$ was evaporated in vacuo to an oil which was applied to a silica gel column. Elution with $CHCl_3$/MeOH (15:1 v/v), combination of appropriate fractions and evaporation in vacuo yielded an oil which was crystallized from $Et_2O$ to give 58.5 mg (0.2 mMol, 20%): mp=169°–170° C.; UV (nm): at pH 1 max=276 (=7400), min=239 (=500); at pH 13 max=274 (=6400), min=249 (=3800); $H^1$NMR (DMSO-$d_6$) 8.29 (s, 1H, H6), 6.05 (t,1H,H1', J=5.5 Hz), 5.49–5.29 (m,1H,5'-OH), 4.44–4.20 (m,1H,H3'), 3.88–3.71 (m,1H,H4'), 3.71–3.53 (m,2H,H5'), 2.63–2.31 (m,2H,H2'); analysis calculated for $C_9H_{10}N_5O_4Cl$:c37.58, H 3.50, N 24.35, Cl 12.32. Found: C 37.67, H 3.54, N 24.39, Cl 12.40.

EXAMPLE 31

5'-Acetyl-3'-azido-3-benzoyl-3'-deoxythymidine

5'-Acetyl-3'-azido-3'-deoxythymidine (0.75 g, 2.4 mMol) was dissolved in pyridine (5 mL) and benzoyl chloride (1.4 mL, 12 mMol, 5 eq.) was added at room temperature. The reaction was stirred overnight then poured onto ice water (250 mL). The pH of the aqueous solution was adjusted to 1. The product was extracted with chloroform. The organic phase was washed with water, dried with $MgSO_4$ and filtered. The chloroform was removed and the oily product was flash chromatographed on silica gel eluted with chloroform. The product was collected as an oil.

NMR was taken in DMSO-$d_6$

NMR: δ8.04–7.50 (m,6H; 3N-benzoyl and 6H), 6.12 (dd,1H, $J_{1',2m'}$=5.6 Hz, $J_{1',2b'}$=6.7 Hz, 1'H), δ4.55–3.96 (m, 4H; 3'H,4'H,5H'), δ2.62–2.38 (m,2H,2'H), δ2.07 (s,3H,5' acetyl $CH_3$), δ1.90 (d, 3H, $J_{5,6}$=1.0 Hz, 5$CH_3$)

CHN calculated for $C_{19}H_{19}H_5O_6$; Calculated: C-55.20; H-4.63; N-16.94. Found: C-55.29; H-4.64; N-16.93.

Preparation of 5'-Esters of threo-3'-Azido-3'-Deoxythymidine

EXAMPLE 32

Threo-3'-Azido-3'-deoxy-5'-O-phenoxyacetylthymidine

Threo-3'-Azido-3'-deoxythymidine (1.0 g, 3.7 mMol) was dissolved in pyridine (10 mL). Water was removed by boiling the solution until the temperature of the vapor coming off reached 115° C. The reaction was chilled to 0° C. The phenoxyacetyl chloride (1 mL, 7.4 mMol, 2 eq.) was added all at once. The reaction was allowed to continue for three hours. After pouring onto ice water (350 mL), the product oiled out of solution. The aqueous phase was decanted and the oil dissolved in ethyl acetate. After drying with $MgSO_4$ and filtering, the solvent was removed. The resultant oil was flash chromatographed on silica gel eluted with chloroform:methanol (40:1, v/v). The product was collected in 15% yield.

NMR taken in DMSO-$d_6$

NMR: δ11.3 (s,1H,3-NH), δ7.50 (d,1H,$J_{6,5}$=1.2 Hz, 6H), δ7.41–6.86 (m, 5H,5=-phenoxy), δ6.10 (dd, 1H; $J_{1',2a'}$=4.5 Hz, $J_{1',2b'}$=7.5 Hz, 1'H), δ4.86 (s,2H,$CH_2$ of 5=-acetyl), δ4.57–4.21 (m,4H; 3'H,4'H,5'H), δ2.75–2.21 (m, 2H,2'H), δ1.79 (d, 3H, $J_{5,6}$=1.0 Hz, 5$CH_3$)

CHN Calculated for $C_{18}H_{19}N_5O_6$; Calculated: C-53.86; H-4.77; N-17.45. Found: C-53.80; H-4.82; N-1735.

EXAMPLE 33

Threo-3'azido-5-bromo-2',3'-dideoxyuridine

Threo-3'-Azido-5-bromo-2',3'-dideoxyuridine was prepared from 2'-deoxyuridine by a five step reaction sequence.

Protection of the 5'-hydroxyl of 2'-deoxyuridine with a triphenylmethyl group was accomplished in the usual manner. (1) the 3'-hydroxyl was mesylated in the usual fashion. (2) An azide was introduced into the 3' position with the correct stereochemistry by adding 2'-deoxy-3'-mesyl-5'-trityluridine (22 g, 40 mMol) to a solution of sodium azide (7.84 g, 120 mMol, 3 eq.) in dimethylformamide (380 mL) at 80° C. The reaction was continued for 35 hours. The solution was poured onto ice water (2 L) and the precipitate collected by filtration. The product was isolated by chromatography on silica gel eluted with chloroform:methanol (1:1, v/v) in 51% yield. The 5'-hydroxyl was deblocked with 80% acetic acid on a steambath for 25 minutes. After cooling, the tritylcarbinol was filtered off. The filtrate was reduced to a thick oil in vacuo. The product was isolated by flash chromatography on silica gel eluted with chloroform:methanol (85:15 v/v). The 5 position of threo-3'-azido-2',3'-dideoxyuridine was brominated by exactly the same procedure as outlined for the bromination of erythro-3'-azido-2',3'-dideoxyuridine.

UV pH 1 max 280,=9400, min 244,=2600
pH 13 max 276=6700, min 251=3700

NMR taken in DMSO-$d_6$

NMR: δ11.86 (s,1H,3-NH), δ8.02 (s,1H,6H), δ5.99 (dd,1H, $J_{1',2a'}$=3.0 Hz; $J_{1',2b'}$=7.5 Hz, 1'H0, δ5.1 (t,1H, $J_{5'CH2}$, 5'OH=5.4 Hz, 5'OH), δ4.49 (m,1H, 3'H), δ4.05 (m,1H,4'H), δ3.71 (m,2H,5'H), δ2.72 (m,1H,2b') δ2.18 (m1H,2a')

CHN calculated for $C_9H_{10}BrN_5O_4$-0.25 $H_2O$-0.1 $C_2H_4O_2$ Calculated: C-32.25; H-3.21; N-20.44; Br-23.32. Found: C-32.17; H-3.21; N-20.33; Br-23.19.

References (1) Zorback, W. Syn. Proc. in Nucleic Acid Chem., 1968, 1, 321
(2) Michelson, A. J. Chem. Soc., 1955, 816

EXAMPLE 34

1-(3'-Azido-2',3'-dideoxy-β-D-erythro-pentofuranosyl)-2-(benzyloxo)-5-methyl-4(1H)-pyrimidinone Sodium (0.4 g, 17.4 mMol, 2.6 eq.) was allowed to react with dry benzyl alcohol (10 mL) for one hour at room temperature. 2,5'-Anhydro-3'-azido-3'-deoxythymidine (1.65 g, 6.6 mMol) was added. The reaction was allowed to continue for one hour. After pouring onto ice water (250 mL), the pH was adjusted to 7 and the aqueous phase was extracted with ethyl acetate. The organic phase was extracted with water (4 times). After drying with $MgSO_4$ the ethyl acetate was removed in vacuo. The resultant oil was chromatographed on silica gel eluted first with ethyl acetate then with ethyl acetate:methanol (9:1 v/v). The product containing fractions were collected and the solvents removed in vacuo yielding an oil. The oil crystallized after covering with ethyl ether.

m.p.=125°-126.5° C.
UV pH 1 unstable
pH 13 max 256,=10700, min 240,=8900
NMR taken in DMSO-$d_6$NMR: $\delta$7.8 (d,1H,$J_{6,5}$=1.2 Hz, 6H), $\delta$7.49-7.38 (m,5H,2-phenyl), $\delta$6.08 (dd,1H,$J_{1',2a'}$=5.0 Hz; $J_{1,2b'}$=7.0 Hz, 1'H), $\delta$5.37 (s, 2H,2CH$_2$), $\delta$5.25 (t,1H,$J_{5'}$CH$_2$, 5'OH=5.4 Hz, 5=OH), $\delta$4.36-4.32 (m,1H,3'H), $\delta$3.85-3.81 (m,1H,4'H), $\delta$3.7-3.58 (m,2H,5'H), $\delta$2.53-2.34 (m,2H,2'H), $\delta$1.82 (d,3H,$J_{5,6}$=1.0 Hz, 5CH$_3$).

CHN calculated for $C_{17}H_{19}N_5O_4$; Calculated: C-57.14; H-5.36; N-19.60; Found: C-57.02; H-5.43; N-19.53.

EXAMPLE 35

5'-Esters of 3'-Azido-3'-deoxythymidine

The following 5'-esters of 3'-Azido-3'-deoxythymidine were prepared in the usual way.

a) 3'-Azido-3'-deoxy-5'-O-toluylthymidine
NMR taken in DMSO-$d_6$
NMR: $\delta$7.95-7.29 (m,5H;bH,cH,6H), $\delta$6.16 (t,1H,1'H), $\delta$4.6-4.4 (m,3H,3'H,5'H), $\delta$4.2-4.0 (m,1H,4'H), $\delta$2.39 (s,3H,dCH$_3$), $\delta$1.63 (s,3H,5CH$_3$).

CHN calculated for $C_{18}H_{19}N_5O_5$; Calculated: C-56.10; H-4.97; N-18.17. Found: C-55.88; H-5.00; N-18.09.

b) 3'-Azido-3'-deoxythmidine-5'-O-(Hydrogen succinate)
NMR taken in DMSO-$d_6$
NMR: $\delta$7.46 (s,1H,6H), $\delta$6.13 (m, 1H, 1'H), $\delta$4.48-4.40 (m, 1H,3'H), $\delta$4.34-4.20 (m,2H,5'H), $\delta$3.99-3.94 (m, 1H,4'H), $\delta$12.78 (s,3H,5CH$_3$)

CHN calculated for $C_{14}H_{17}N_5O_7$=0.25 H$_2$O, 0.3 CH$_3$CO$_2$H; Calculated: C-44.98; H-4.83; N-17.96. Found: C-44.90; H-4.77; N-17.85.

c) 3'-Azido-3'-Deoxy-5'-Mesylthymidine
NMR taken in DMSO-$d_6$
NMR: $\delta$7.49 (d,1H,$J_{6,5}$=1.0 Hz, 6H), $\delta$6.15 (t,1H,$J_{1',2'}$=6.6 Hz, 1'H), $\delta$4.54-4.41 (m,3H;3'H,5'H), $\delta$4.14-4.02 (m,1H,4'H), $\delta$3.24 (s,3H,5'-mesyl CH$_3$), $\delta$1.79 (d,3H,$J_{5,6}$=1.0 Hz, 5CH$_3$).

CHN calculated for $C_{11}H_{15}N_5O_6S$; Calculated: C-38.25; H-4.37; N-20.28; S-9.28. Found: C-38.15; H-4.38; N-20.19; S-9.30 d) 3'-Azido-5'-O-(3-Chlorobenzoyl)-3'-Deoxythymidine
NMR taken in DMSO-$d_6$
NMR: $\delta$11.37 (s, 1H,3-NH), $\delta$7.98-7.43 (m,5H;5'-phenyl,6H), $\delta$6.17 (dd,1H; $J_{1',2a'}$=6.1 Hz, $J_{1'2b'}$=7.2 Hz,1'H), $\delta$4.68-4.48 (m,3H;3'H,5'H), $\delta$4.14-4.11 (m,1H,4'H), $\delta$2.48-2.41 (m,2H,2'H), $\delta$1.64 (d,3H,$J_{5,6}$=1.2 Hz, 5CH$_3$)

CHN calculated for $C_{17}H_{16}ClN_5O_5$: Calculated: C-50.31; H-3.97; N-17.26; Cl-8.74. Found: C-50.16; H-4.03; N-17.13;Cl-8.66.

EXAMPLE 36

1-(3'-Azido-2',3'-deoxy-β-D-threo-pentofuranosyl)-2-ethoxy-5-methyl-4(1H)-pyrimidinone Threo-3'-Azido-5'-O-mesylthymidine (1.08 g, 3.13 mMol)(prepared according to a standard method (1) from threo-3'-azidothymidine) was dissolved in 100 mL EtOH and treated with NaHCO$_3$ (0.26 g, 3.13 mMol) at reflux for 18 hours. The reaction was cooled and filtered. The solvents were removed in vacuo and the residue placed on a silica gel column followed by elution with 9:1 (v/v) CHCl$_3$/MeOH. Combination of appropriate fractions and removal of solvents in vacuo yielded 0.7 g (2.4 mMol, 75.7%). mp=120°-122° C.; UV (nm): at pH 1 λ max=260 ($\epsilon$=9300), λ min=237 ($\epsilon$=5500), λ shoulder=221 ($\epsilon$=7500); at pH 13 λ max=256 ($\epsilon$=10000), λ min=240 ($\epsilon$=7700); H$^1$NMR (DMSO-$d_6$) $\delta$7.58 (s,1H,H6), $\delta$6.0 (dd,1H,H1', J=2.9, 4.56 Hz) $\delta$5.06 (t,1H,5=OH, J=4.91 Hz), $\delta$4.51-4.47 (m,1H,H3'), $\delta$4.34 (q, 2H,—CH$_2$—, J=7.14 Hz), $\delta$4.10-4.05 (m,1H,H4'), $\delta$3.73 (t,2H,H5', J=5.62 Hz), $\delta$2.82-2.73 (m, 1H,H2'b), $\delta$2.21-2.14 (m,1H,H2'a), $\delta$1.82 (s,3H,5 CH$_3$), $\delta$1.31 (t,3H,—CH$_2$—CH$_3$, J=6.65 Hz). Analysis calculated for $C_{12}H_{17}N_5O_4$: C 48.81, H 5.80, N 23.72
Found: C 48.59, H 5.86, N 23.64.

(1) J. Horwitz et al. J. Org. Chem. (1964), 29, 2076.

EXAMPLE 37

Threo-3'-Azido-3'-deoxy-4-thiothymidine

Threo-3'-Azido-5'-O-trityl-4-(1,2,4-triazole)thymidine (1.25 g, 2.2 mMol) (1) was dissolved in 100 mL acetone and 30 mL H$_2$O then treated with 0.22 g NaSH.xH$_2$O. The mixture was stirred 3 hours. The volume was reduced by half and extracted with 300 mL CHCL$_3$. The CHCl$_3$ was washed with 50 mL H$_2$O, dried over Na$_2$SO$_4$, then removed by dissolving this oil in 100 mL 80% HOAc. The solution was heated on a steam bath for 2 hours then cooled, diluted with 100 mL H$_2$O and filtered. The solvents were removed in vacuo and the oil placed on a silica gel column. Elution with 20:1 (v/v) CHCl$_3$ MeOH, collection of appropriate fractions followed by removal of solvents in vacuo yielded 0.18 g (0.62 mMol; 28%). mp=65°-67° C.; UV (nm): at pH 1λmax=337 ($\epsilon$=20700), λ min=280 ($\epsilon$=1200), λ shoulder=238 (λ=3400); at pH 13 λ max=320 (λ=18400), λmin=257 ($\epsilon$=1700); H'NMR (DMSO-$d_6$) $\delta$7.63 (s,1H,H6) $\delta$5.97 (dd, 1H,H1', J=5.61 Hz), $\delta$2.78-2.68 (m,1H,H2'b), $\delta$220-2.14 (m,1H,H2's), $\delta$2.00 (s,3H,5CH$_3$). Analysis calculated for $C_{10}H_{13}N_5O_3S$ 0.1 $C_2H_6O$ 0.25 H$_2$O: C 41.90, H 4.86, N 23.95, S10.97 Found: C 41.99, H 4.73, N 23.88, S 10.91.
1) W. Sung Nucleic Acids Research (1981), 9, 619.

We claim:

1. A method of treating idiopathic thrombocytopaenia purpura in a human in need thereof, which comprises administering to said human an effective thrombocytopaenia purpura treatment amount of a compound 3'-azido-3'-deoxythmidine.

2. The method of claim 1, in which said compound is administered orally.

3. The method of claim 1, in which said compound is administered parenterally.

4. The method of treating a patient diagnosed as having thrombocytopaenia purpura, which comprises orally or intravenously administering an effective thromocytopaenia purpura treatment amount of 3'-azido-3'-deoxythymidine to said patient.

5. A method of increasing platelets in a patient in need thereof, which comprises administering an effective platelet increasing amount of 3'-azido-3'-deoxythymidine to said patient.

* * * * *